(12) United States Patent
Yoo et al.

(10) Patent No.: US 8,136,943 B2
(45) Date of Patent: Mar. 20, 2012

(54) TESTING/TRAINING VISUAL PERCEPTION SPEED AND/OR SPAN

(75) Inventors: Herb Yoo, Beaverton, OR (US);
Graham B. Erickson, Hillsboro, OR (US); Alan W. Reichow, Beaverton, OR (US)

(73) Assignee: Nike, Inc., Beaverton, OR (US)

( * ) Notice: Subject to any disclaimer, the term of this patent is extended or adjusted under 35 U.S.C. 154(b) by 0 days.

(21) Appl. No.: 12/500,403

(22) Filed: Jul. 9, 2009

(65) Prior Publication Data
US 2011/0007268 A1    Jan. 13, 2011

(51) Int. Cl.
*A61B 3/00* (2006.01)

(52) U.S. Cl. .................... 351/203; 351/238; 351/246

(58) Field of Classification Search .............. 351/200, 351/203, 222, 223, 237, 238, 246
See application file for complete search history.

(56) References Cited

U.S. PATENT DOCUMENTS

| | | | |
|---|---|---|---|
| 3,861,790 A | 1/1975 | Tamura | |
| 5,050,982 A | 9/1991 | Meissner | |
| 5,478,239 A | 12/1995 | Fuerst | |
| 6,409,513 B1 * | 6/2002 | Kawamura et al. | 434/178 |
| 6,755,525 B2 | 6/2004 | Reichow | |
| 6,811,258 B1 | 11/2004 | Grant | |
| 6,893,127 B2 | 5/2005 | Reichow | |
| 7,073,208 B2 | 7/2006 | Penque, Jr. | |
| 2010/0182565 A1 * | 7/2010 | Reichow et al. | 351/203 |

OTHER PUBLICATIONS

Reichow, et al., "Introduction to Behavioral Optometry", Sports Vision, 1993, 75 pages, Optometric Extension Program Foundation, United States.

Ferreira, "An Overview of Research in Sports Vision: its History and an Optometric Perspective", The South African Optometrist, Dec. 2003, pp. 142-149, vol. 62, No. 4, Auckland Park, South Africa.

Coffey, et al., "Visual Performance Enhancement in Sports Optometry", Sports Vision 1995, pp. 158-177, Butterworth-Heinermann, United States.

Cardall, "Contact Lenses in Sport: a General Overview", Optician, Jan. 13, 2006, pp. 22-25, vol. 231, No. 6034, United States.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Koenig, "Practicing Perception: Eyes Can Be Trained to be More Effective", USA Today Baseball Weekly, 1996, 3 pages, United States.

(Continued)

*Primary Examiner* — Huy K Mai
(74) *Attorney, Agent, or Firm* — Shook, Hardy & Bacon L.L.P.

(57) ABSTRACT

System and methods for testing and/or training a subject's visual perception span and/or speed are provided. More specifically, a method may include testing/training various aspects of the subject's visual perception span/speed through the use of assessments that test the subject's ability to receive and retain information that is flashed in front of them. By using various assessments, an efficient examination may be administered. In accordance with the invention, an individual may be subjected to such a method of testing/training comprising: presenting one or more two-dimensional representations to the subject at a first time; receiving input responses from the subject at a second time; and processing the received input responses to provide a measure of the perception span of the subject; and processing the time between the first time and the second time to provide a measure of the perception speed of the subject.

22 Claims, 11 Drawing Sheets

OTHER PUBLICATIONS

Coffey, et al., "Optometric Evaluation of the Elite Athlete," Problems in Optometry, Mar. 1990, pp. 32-59, vol. 2, No. 1, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

* cited by examiner

TESTING/TRAINING VISUAL PERCEPTION SPEED AND/OR SPAN

STATEMENT REGARDING FEDERALLY SPONSORED RESEARCH OR DEVELOPMENT

Not applicable.

TECHNICAL FIELD

The present invention relates generally to the test of an individual's visual perception span.

BACKGROUND

Along with physical ability, an individual's visual and related skills play a significant role in the individual's performance when participating in an activity, such as a sport. Typically, to improve in the sport or activity, an individual will focus on improving his or her physical ability to elevate his or her overall performance. Improving a physical ability may require, first, that an individual's ability be accurately tested. After evaluating, an individual may undergo a training regime wherein the individual is (1) tested, (2) trained, and (3) tested again. This procedure is continued as necessary until the individual achieves and/or maintains the desired level of aptitude in an area.

SUMMARY

Embodiments of the invention are defined by the claims below, not this summary. A high-level overview of various aspects of the invention are provided here for that reason: to provide an overview of the disclosure and to introduce a selection of concepts in a simplified form that are further described below in the Detailed Description. This summary is not intended to identify key features or essential features of the claimed subject matter, nor is it intended to be used as an aid in isolation to determine the scope of the claimed subject matter.

In accordance with the invention, systems and methods for testing and/or training a subject's visual perception speed and/or span are provided. In accordance with the invention, the visual perception span of an individual may be tested or trained using systems and/or methods to present one or more two-dimensional representations to the individual, receive inputs from the individual based upon the individual's perception of the one or more two-dimensional representations, and process the received input(s). Visual perception span tests may be configurable so that the assessments administered may vary based on the needs of the individual. The received input may then, for example, be used to compute data related to the individual's visual perception span, both overall and for each individual assessment. Further, the visual perception speed of an individual may be tested by determining how quickly an individual can perceive one or more two-dimensional representations. The visual perception span and/or speed of an individual may be trained using similar systems and/or methods.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Embodiments of the present invention provide systems and methods for testing and/or training an individual's visual perception span and/or speed. Traditionally, visual perception span was measured using a tachistoscope. A tachistoscope displays an image on a screen for a defined brief period of time, typically by projecting an image on a screen. A traditional tachistoscope may be used to present spatially arranged indicia in accordance with the present invention, although any other type of display device may be used. In embodiments of the present invention, a number of indicia may be presented in a spatial arrangement on a display screen for a predetermined amount of time. The indicia may convey information for perception by the subject, such as the arrangement of the indicia, the traits of the indicia, etc. After the predetermined amount of time, the indicia may cease to be displayed and the individual may be prompted to provide a response based upon the indicia previously displayed. Indicia may be characterized by various sizes, colors or other distinctions, and different characteristics may correspond to different correct inputs. The amount of information displayed at a single time may be varied to obtain a measure of the visual perception span of a subject. The time duration for which indicia are displayed may be varied to obtain a measure of the visual perception speed of a subject. Accordingly, visual perception span and/or speed may be determined by comparing inputs provided by an individual in response to the visual stimuli. In embodiments, a user's action and a user's lack of an action may each be understood as an input.

Figure 1:
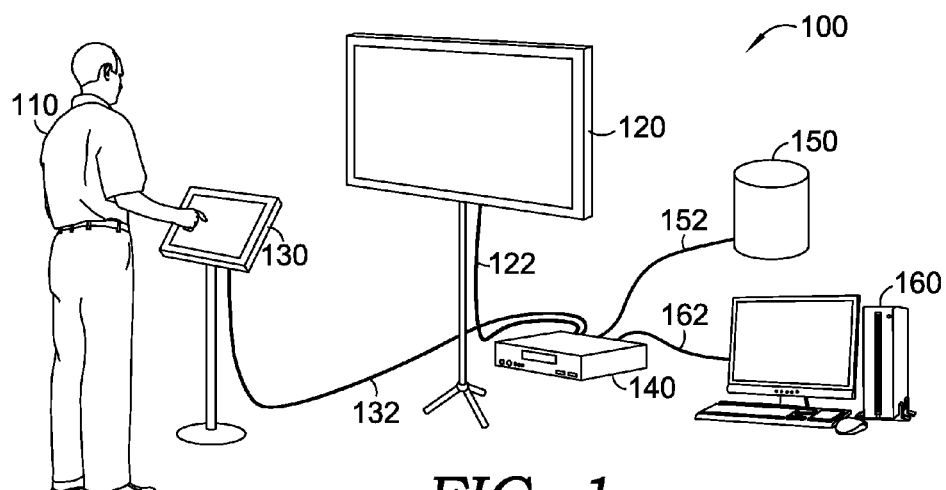
FIG. 1 illustrates an exemplary visual perception span and/or speed testing and/or training system in accordance with an embodiment of the present invention.

Referring to the drawings in general, and initially to FIG. 1 in particular, an exemplary system for testing and/or training the visual perception span and/or speed of a subject in accordance with an embodiment of the present invention is illustrated and designated generally as system 100. System 100 shown in FIG. 1 is merely an example of one suitable testing/training system environment and is not intended to suggest any limitation as to the scope of use or functionality of embodiments of the present invention. Neither should system 100 be interpreted as having any dependency or requirement of any single component or combination of components illustrated therein.

System 100 may be used to test or train the visual perception span and/or speed of subject 110. System 100 may include display device 120, connection 122, touch-sensitive screen 130, connection 132, test unit 140, database 150, connection 152, computer 160 and connection 162. While test unit 140 is referred to as "test unit" or "testing unit" herein, test unit 140 may be used for both testing and/or training. The various components of testing system 100 may communicate through connection 122, 132, 152, and/or 162. Connection 122, 132, 152, and/or 162 may be made by wire (such as a cable), or wireless (such as a wireless network, Bluetooth protocol, etc.). Connection 122, 132, 152, and/or 162 may also be a network, where the network may include, without limitation, one or more local area networks (LANs) and/or wide area networks (WANs). Such networking environments are commonplace in enterprise-wide computer networks, intranets, and the Internet. Further, connection 122, 132, 152, and/or 162 may comprise a locally wired connection between components of testing system 100. Any media or protocol may be used for connection 122, 132, 152, and/or 162. Accordingly, connection 122, 132, 152 and 162 are not further described herein.

Touch-sensitive screen 130 may be capable of receiving one or more responses from subject 110 as a touch input. Touch-sensitive screen 130 may be any device that may receive touch-based responses from subject 110. It should be noted that the present invention is not limited to implementation of touch-sensitive screen 130 input device, but may be implemented on any of a variety of different types of input devices within the scope of embodiments hereof. Further, touch-sensitive screen 130 and display device 120 may comprise a single device that both displays information to subject 110 and receives inputs from subject 110. More than one input device, such as touch-sensitive screen 130, may be used with testing system 100. An alternative input device or devices may comprise, for example, a microphone, joystick, game pad, keyboard, keypad, game controller, gesture recognition system, and/or any other input-initiating component with at least binary distinguishing capabilities that may provide wired or wireless data to an input device in response to information displayed to subject 110 by display device 120.

An input device may also or alternatively comprise voice recognition equipment and/or software that processes auditory inputs from a test subject. For example, the auditory input from the subject, in order to show recognition of the visual indicia, may be a verbalization of the characteristics, such as location, possessed by the visual indicia displayed on display device 120.

If an input device is a gesture recognition system, a variety of systems and/or methods may be used to receive inputs. For example, one or more cameras may be used to monitor the movement of a subject's body limbs and/or extremities and, in conjunction with appropriate hardware and/or software, register an input when subject makes an appropriate gesture. Gesture recognition systems may also utilize optical markers attached to subject to facilitate motion tracking. Transmitters attached to subject 110 and receivers (for example, utilizing radio infrared, sonic, subsonic, or ultrasonic transmissions) may also be utilized as part of a gesture recognition system.

If an input device is touch-sensitive screen 130, any type of touch-sensitive screen may be utilized. Also, an overlay of a touch-sensitive material may be used to receive touch inputs in conjunction with a display that is not itself touch-sensitive. Such an overlay may be any distance from the display.

Display device 120 may be capable of displaying information to subject 110 as output images and/or video visually observable by a subject and may be any type of computer, testing apparatus, or television monitor, including cathode ray tube, liquid crystal display, plasma screen, or any other display type. Also or alternatively, display device 120 may comprise one or more screens upon which images are projected, either from the front or from the rear. Further, display device 120 may provide a subject interface for an administrator to interact with the test unit 140 before, during, and after administering visual perception span assessments to test subject 110.

In operation, display device 120 may be configured to present visual information to subject 110 in the form of one or more visual indicia to a test subject. As discussed more fully below, display device 120 may present visual indicia possessing varying amounts of information to test and/or train the visual perception span of subject 110. In general, each of the visual indicia may possess a trait or traits. A trait may be, for example, a spatial location, one of a predetermined number of mutually exclusive traits (e.g., an indicator that faces either up, down, left, or right), a color, etc., or any combination of traits. Alternatively, other traits may be used. The present invention is not limited to any particular trait. Further, as discussed more fully below, display device 120 may present visual information to subject 110 for varying amounts of time to test and/or train the visual perception speed of subject 110.

Display device 120 may be any type of monitor, display goggles or visor, screen and projector, or other device capable of displaying an image. By way of further example, display device 120 may be an apparatus that uses minor and/or lenses strategically placed to generate a visual perspective of distance within a limited spatial area (e.g., providing a configuration of mirrors to produce a tunnel effect). An example of such an apparatus is a perspective testing apparatus utilizing mirrors to generate a perspective of distance. Further, multiple display devices, of the same or different types, may be used.

Alternatively, display device 120 may provide one or more three-dimensional images to the test subject. The three-dimensional image display may include virtual reality or holographic presentations to the subject. In responding to one or more three-dimensional images, a test subject may utilize gesture-tracking technologies that may input coordinates of a test subject's movements in response to the one or more three-dimensional images. For instance, a test subject may be shown a set of three-dimensional holographic images within a cube structure. In response to the three-dimensional images, the test subject may use a gesture-tracking glove to indicate the associated location of the images as they would be positioned in a relative, but smaller, input device. In this way, the test subject may indicate the relative positions of one or more three-dimensional images in a three-dimensional format.

Test unit 140, as shown in FIG. 1, may be any type of computing device. Database 150 may be configured to store information associated with assessments of visual perception span. The information stored in database 150 may be configurable and may include any information relevant to testing and/or training visual perception span and/or speed of individuals, such as information describing the displayed indicia and received inputs for one or more iteration of testing/training methods, measures of the accuracy and/or speed of subject's response, etc.

The information stored in database 150 may also comprise the scores and assessments of subject 110 and/or other individuals. The scores and assessments of subject 110 may be used in selecting and/or designing an individualized visual perception span/speed training program for the subject 110, and/or to select a protocol to test the visual perception span/speed of subject 110. For example, if an individual is scoring very well on his assessments, it may be beneficial to test/train him using more advanced and/or difficult tests/training programs. Testing/training may be more difficult in that more information is displayed and/or for less time. Although illustrated as a single, independent component, database 150 may, in fact, be a plurality of databases, for instance, a database cluster. Further, portions or the entirety of database 150 may reside on a computing device associated with test unit 140, another external computing device (not shown), and/or any combination thereof. Database 150 may be optional and need not be implemented in conjunction with testing system 100.

Figure 2:
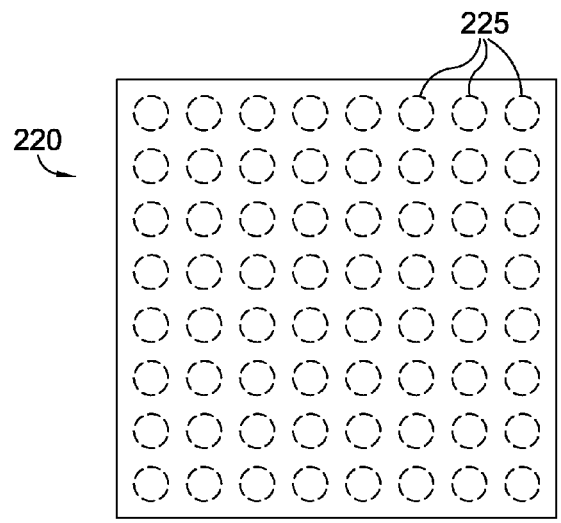
FIG. 2 illustrates a display device that provides visual information in accordance with an embodiment of the present invention.

Referring now to FIG. 2, display device 220 is further illustrated in accordance with an embodiment of the present invention. Display device 220 may comprise a plurality of portions 225. Portions 225 presented in FIG. 2 are shown in an inactive state. Portions 225 may be lightbulbs, elements, portions of a screen, or other materials with the ability to indicate a distinction between an active state and an alternative state, such as an inactive state. Portions 225 of display device 220 may be arranged in a two-dimensional representation. Portions 225 may also or alternatively comprise more than one color, wherein the more than one color of portions may be used to distinguish between active and inactive states. In another embodiment, an "active" portion may comprise a lightbulb that is on whereas an "inactive" portion may comprise a lightbulb that is off. The activation status of portions 225 of display device may determine, the amount of information provided to a subject by display device 220, and the duration of the activation of portions 225 of display device 220 may determine the time available for a subject to perceive information displayed. As presented in FIG. 2, each portion 225 is in an "inactive" state.

Figure 3:
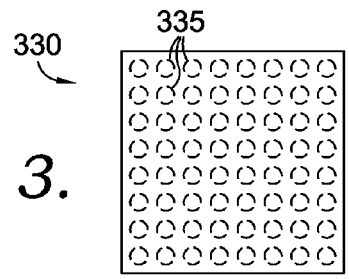
FIG. 3 illustrates an input device that receives inputs in response to visual information in accordance with an embodiment of the present invention.

FIG. 3 illustrates input device 330 in accordance with an embodiment of the present invention. Input device 330 may comprise a plurality of portions 335. The plurality of portions comprising input device 330 may correspond to the plurality of portions comprising display device 220 as shown in FIG. 2 Input device 330 and display device 220 may comprise a single touch-sensitive screen. Portions 335 of input device 330 may be arranged in a two-dimensional representation that corresponds to the associated display device 220, or may be of a different dimension of an associated display device so as to be compatible with multiple dimensions of display devices.

Figure 4:
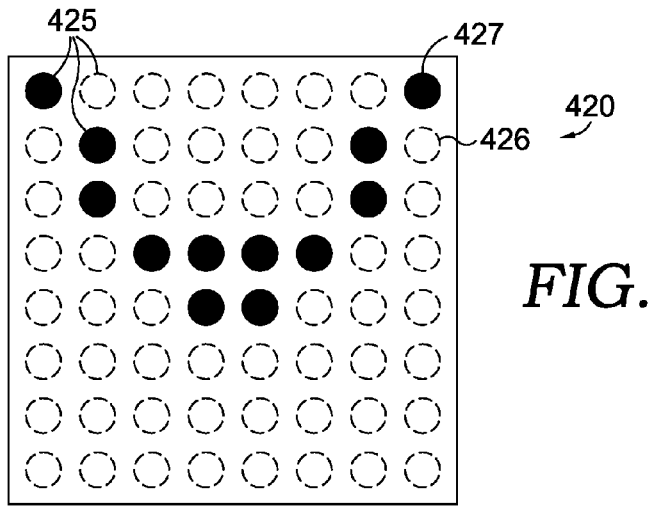
FIG. 4 illustrates another display device that provides visual information in accordance with an embodiment of the present invention.

Referring to FIG. 4, display device 420 is further illustrated in accordance with an embodiment of the present invention. Display device 420 may be similar to display device 220 as indicated in FIG. 2. As such, display device 420 may comprise a plurality of portions 425. FIG. 4 further illustrates a distinction between active portions 427 and inactive portions 426. In addition to active portions 427, inactive portions 426 are represented as comprising the rest of the grid on display device 420, wherein inactive portions 426 may be represented by their empty characteristic.

Figure 5:
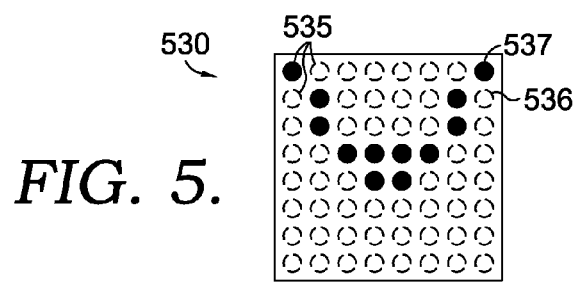
FIG. 5 illustrates another input device that receives inputs in response to visual information in accordance with an embodiment of the present invention.

FIG. 5 illustrates input device 530 in accordance with an embodiment of the present invention. Input device 530 and display device 420 may comprise a single touch-sensitive screen. As shown in FIG. 5, input device 530 has been used to indicate a test subject's response inputs, for example, in response to the stimuli displayed on display device 420. Input device 530 may comprise portions 535, wherein portions may be classified as active portions 536 and inactive portions 537. The portions 535 in FIG. 5 may be similar to the portions 225 as indicated in FIG. 2.

The response inputs may be entered by a test subject in response to stimuli from at least one display device, such as display device 120 illustrated in FIG. 1. Input device 530 may be a touch-screen device. Input device 530 may be placed within sight of a display screen, or input device 530 may be in an alternative location, such as a different room, such that a subject must move to another location to enter an input in response to displayed information. In another alternative, the placement of input device 530 may be independent of the placement of a display device.

Figure 14A:
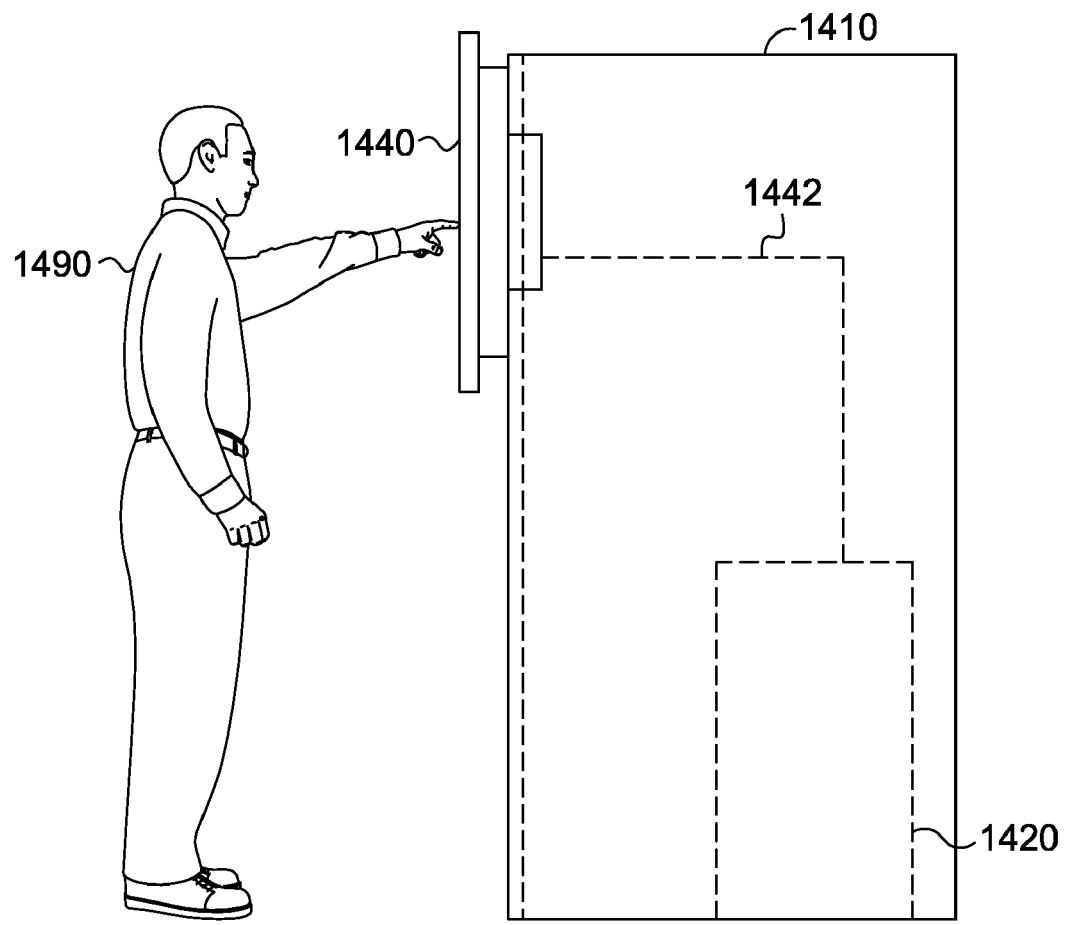
FIGS. 14A-14C illustrate an embodiment of the invention utilizing a single touch sensitive display device as both a display device and as an input device.
Figure 14B:
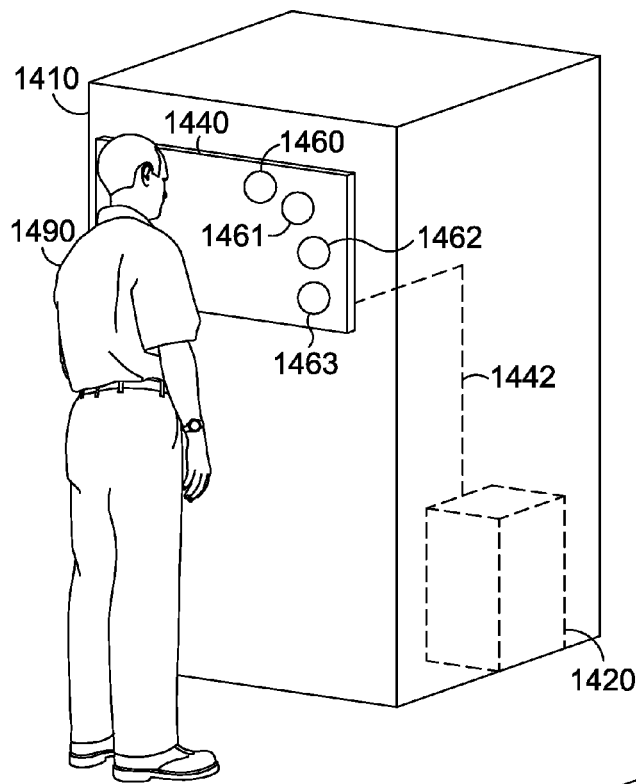
Figure 14C:
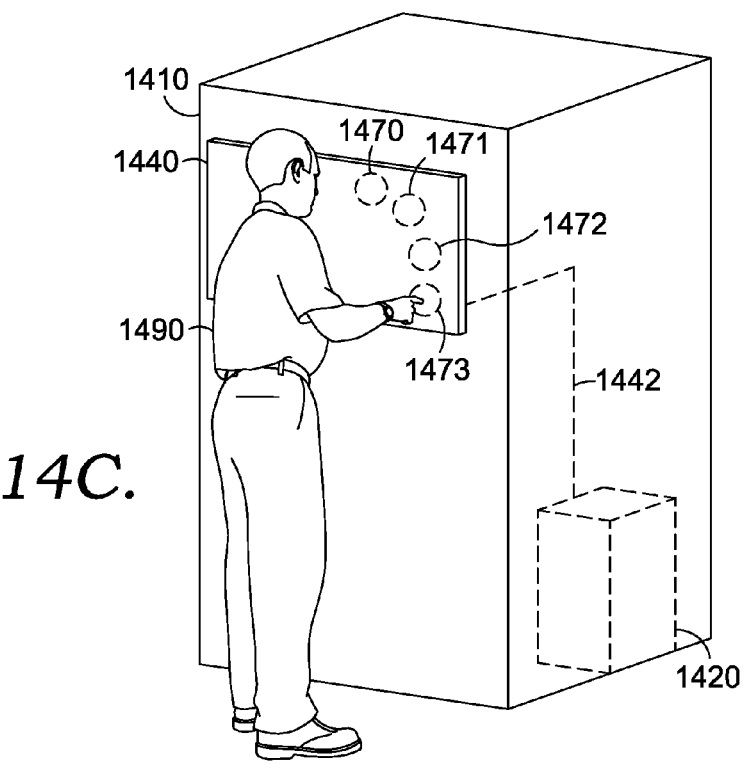

By varying the size and/or position of input device 530 relative to the associated display device "retina burn" or "sensory memory" may be avoided. Sensory memory can produce "ghost" images of indicia after their display has ceased and, consequently, may be used to facilitate the correct input. In many instances, however, testing and/or training visual perception span and/or speed of a subject in a fashion that accounts for the sensory memory of a subject may be desired. In such an instance, a similarly sized and/or positioned display device and input device, or a single touch-sensitive screen to serve as both a display device and an input device, may be used. An example of a system utilizing a single touch-sensitive screen is illustrated in FIGS. 14A-14C, which are described in greater detail below.

Figure 6:
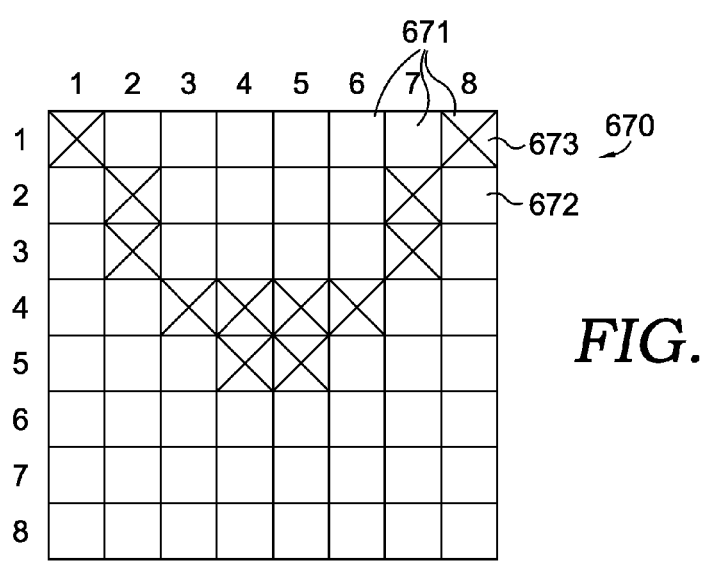
FIG. 6 depicts a visual perception span assessment in accordance with an embodiment of the present invention.

Referring to FIG. 6, a visual perception span and/or speed assessment 670 is illustrated in accordance with an embodiment of the present invention. FIG. 6 depicts the accuracy of a subject's inputs in response to displayed visual information which may be used to test and/or train the visual perception span and/or the subject. FIG. 6 illustrates a collection of input squares 671 that may have been used to indicate portions selected by the test subject. As seen in FIG. 6, blank input squares 672 indicate areas where the test subject did not enter an input. In contrast, non-blank input squares, such as square 673, indicate areas where the test subject did enter an input. As shown in FIG. 6, all non-blank input squares are indicated as correct input squares, similar to square 673. Correct input squares may be marked with an "X" to indicate the test subject has entered an accurate input into an input device in response to one or more images presented on a display device. Such a visual characterization of a subject's test result as illustrated in FIG. 6 may not be needed or desired as part of the testing and/or training of the visual perception span and/or speed of a subject, but is presented to facilitate the description of the present invention.

Figure 7:
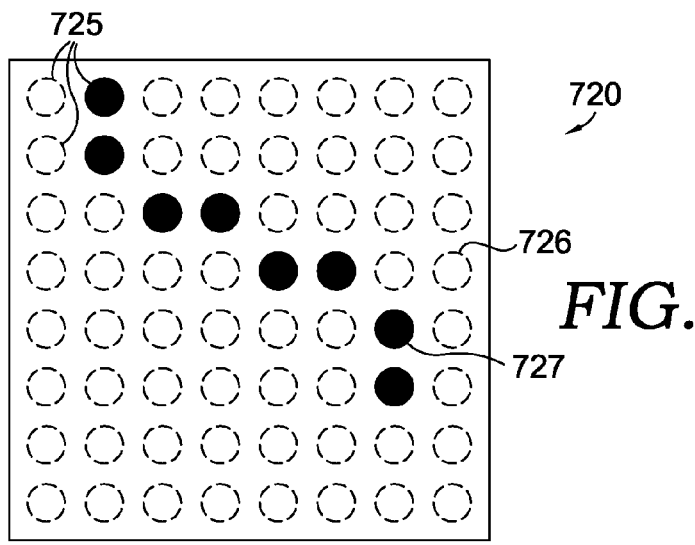
FIG. 7 illustrates a further display device that provides visual information in accordance with an embodiment of the present invention.

FIG. 7 depicts a further illustration of display device 720 in accordance with an embodiment of the present invention. Display device 720 may be similar to display device 420 as seen in FIG. 4, and may present visual information to a subject. Display device 720 may comprise a plurality of portions 725. Similar to FIG. 4, FIG. 7 further illustrates a distinction between active portions 727 and inactive portions 726. In distinguishing between portions 725, FIG. 7 illustrates a two-dimensional representation of active portions 727. In addition to active portions 727, inactive portions 726 are represented as comprising the rest of the grid on display device 720. In alternative embodiments, the distinctions between portions need not be limited to binary characteristics, such as filled-in portions vs. empty portions. In alternative embodiments, portions may be distinguished based on a number of factors across portions. For example, four categories of portions may be distinguished based on two characteristics such as those seen in cards: portions that are red vs. portions that are black, and an additional distinction between portions that are diamonds, hearts, clubs and spades, the embodiment leaving open the possibility for examples such as red spades and black diamonds.

Figure 8:
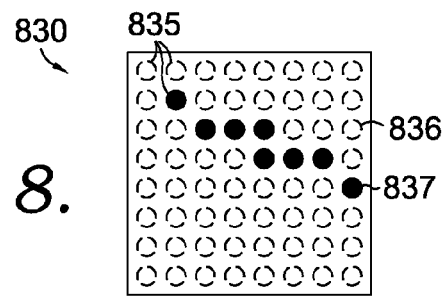
FIG. 8 illustrates an input device that receives inputs in response to visual information in accordance with a further embodiment of the present invention.

FIG. 8 illustrates an input device 830 in accordance with the present invention. Input device 830 and display device 720 may comprise a single touch-sensitive screen. Input device 830 may be used by a subject to enter inputs in response to stimuli, such as those illustrated on display device 720 in FIG. 7. Input device 830 may comprise a plurality of portions 835. Similar to FIG. 4, FIG. 8 further illustrates a distinction between active portions 837 which have been touched by subject and inactive portions 836. As shown in FIG. 8, input device 830 reflects a test subject's inputs. When the two-dimensional input representation of FIG. 8 is compared against the two-dimensional input representation of FIG. 7, it is seen that the test subject's responsive input as seen in FIG. 8 is of a different form than the two-dimensional display as shown in FIG. 7.

Figure 9:
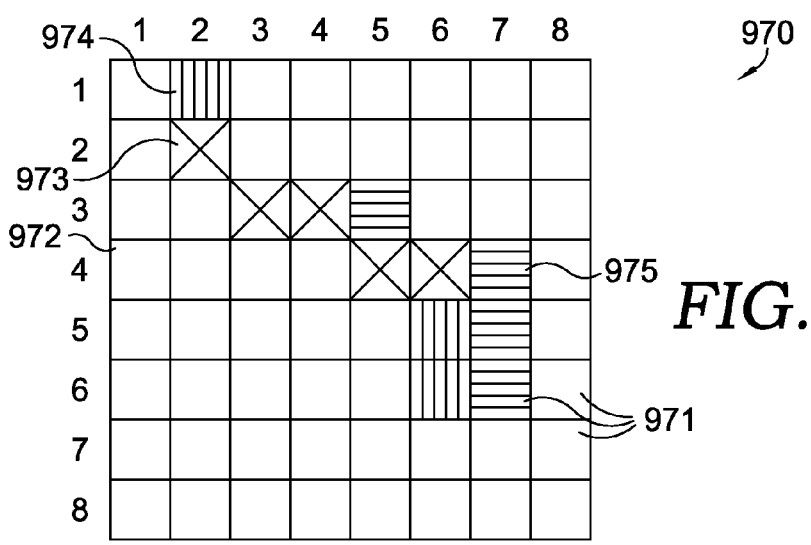
FIG. 9 depicts a representation of a visual perception span assessment in accordance with a further embodiment of the present invention.

FIG. 9 illustrates a visual perception span and/or speed assessment 970 that compares the output depicted in FIG. 7 to the input depicted in FIG. 8 in accordance with an embodiment of the present invention. FIG. 9 is similar to FIG. 6 insofar as it also depicts a comparison of the inputs received from a subject in response to visual information displayed to a subject. In contrast to FIG. 6, however, FIG. 9 depicts a scenario wherein some of the responses input by the subject are incorrect in comparison to the visual information illustrated in FIG. 7. Similar to FIG. 6, FIG. 9 illustrates input squares 971 that indicate areas where the subject did not enter an input in response to visual information displayed by a display device. FIG. 9 illustrates blank input squares, such as square 972, and non-blank input squares, such as squares 973, 974 and 975, that indicate areas where the subject did enter an input in response to visual information displayed by a display device or where the test subject failed to enter a response at a location corresponding to visual information displayed by a display device.

Non-blank squares are illustrated with different symbols to indicate whether the subject correctly registered an input. As shown in FIG. 9, some non-blank squares indicate a correct input, such as square 973. Correct input squares are illustrated with an "X" to indicate that the subject entered an accurate input into an input device in response to visual information presented on a display device. As also shown in FIG. 9, some non-blank squares indicate incorrect input squares, such as squares 974 and 975. Incorrect input squares similar to square 975 are shown with vertical lines to indicate the test subject failed to enter a response in that portion of input device 830 corresponding to an active indicia on the display device 730. Incorrect input squares similar to square 974 are shown with horizontal lines to indicate the subject entered an input on a portion of input device 830 that did not reflect the correct location on at image as seen on the display device. The illustration of FIG. 9 and the examples of indication markers as described above are examples only, and are not meant to limit the breadth of the invention. Further, a visual characterization of a subject's test result may not be needed or desired, and is illustrated to facilitate understanding of the present invention.

Figure 10:
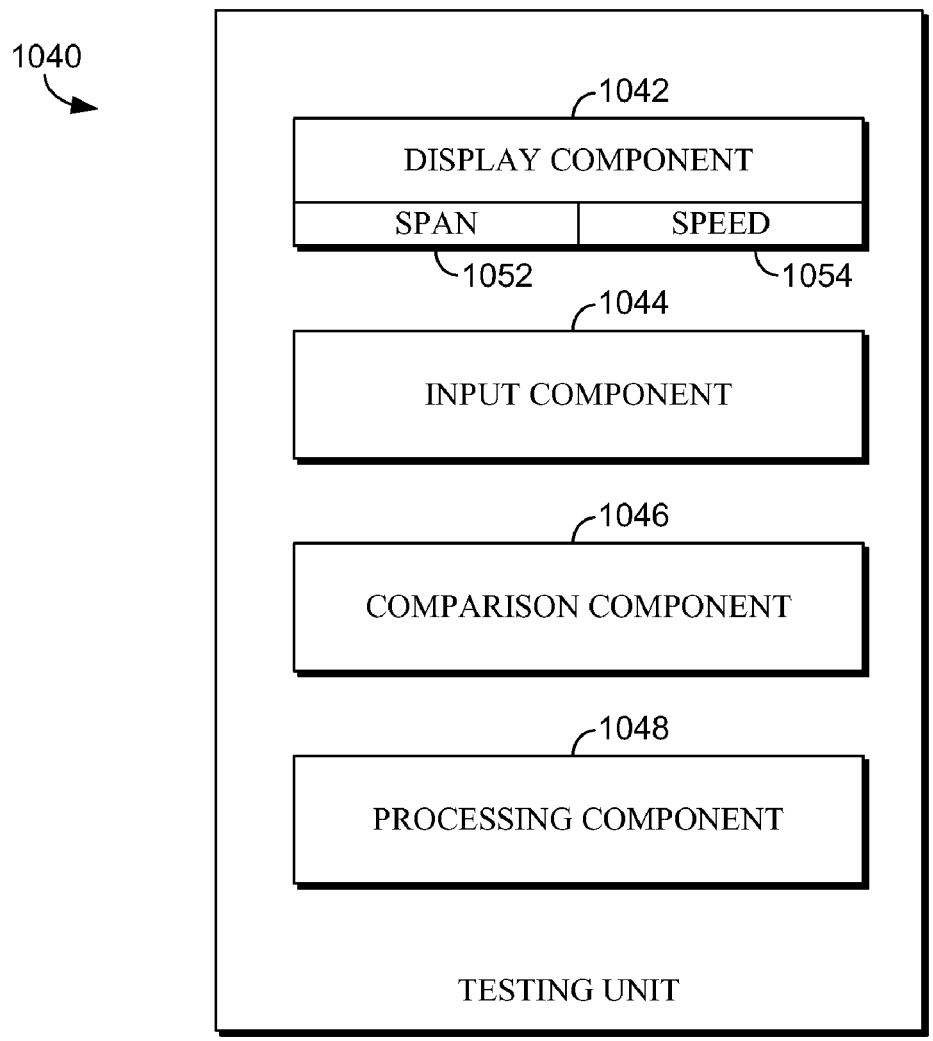
FIG. 10 illustrates a testing unit in accordance with an embodiment of the present invention.

FIG. 10 illustrates a testing unit 1040 in accordance with an embodiment of the present invention. While referred to as "testing unit" or a "test unit" herein, testing unit 1040 may be used for both testing and/or training the visual perception span and/or speed of a subject. As shown in FIG. 10, testing unit 1040 may comprise a display component 1042 with a span component 1052 and a speed component 1054, an input component 1044, a comparison component 1046, a processing component 1048, and/or any other type of visual test component. Components 1042, 1044, 1046, 1048, 1052, and 1054 illustrated in FIG. 10 are exemplary in nature, number, and relationship and should not be construed as limiting. Components 1042, 1044, 1046, 1048, 1052, and 1054 may comprise software operating on one or more general purpose or special purpose computer, specialized circuitry, other type of computing device, or a combination thereof. Further, each of components 1042, 1044, 1046, 1048, 1052, and 1054 may comprise different software and/or hardware, the same software and/or hardware, and/or a different combination of software and/or hardware. Components 1042, 1044, 1046, 1048, 1052, 1054 may comprise discrete components or subcomponents in any combination. Any number of components may be employed to achieve the desired functionality within the scope of embodiments of the present invention. Each of these components may be used by testing unit 1040 to test various aspects of an individual's visual perception span abilities.

Display component 1042 may be configured to present visual information on a display device to test and/or train the visual perception span and/or speed of a subject. Any visual indicia may be used, including those described herein. The visual information may be visual indicia presented using a display device, such as display device 130 represented in FIG. 1. Display component 1042 may further comprise a span Component 1052 that controls the amount of visual information displayed and speed component 1054 that controls the amount of time during which visual information is displayed. Input component 1044 may be configured to track the responses of a test subject registered at an input device, such as test subject 110 and input device 130 illustrated in FIG. 1.

Comparison component 1046 may be configured to evaluate the inputs received from a subject in comparison to the displayed visual information as part of testing and/or training the visual perception span and/or speed of a subject. Comparison component 1046 may be used to compare the differences between a displayed set of indicia, such as image 720 shown in FIG. 7, and the response of subject, such as input 830 as shown in FIG. 8. Processing component 1048 may be configured to process information such as the accuracy of the response of a subject such as determined by comparison component 1046, the amount of information displayed to a subject, such as by span component 1052, the amount of time information was displayed to a subject, such as by speed component 1054, information regarding the prior performance of the subject or other individuals, such as may be stored in a database that may be maintained on storage device 150 illustrated in FIG. 1, etc.

Figure 11:
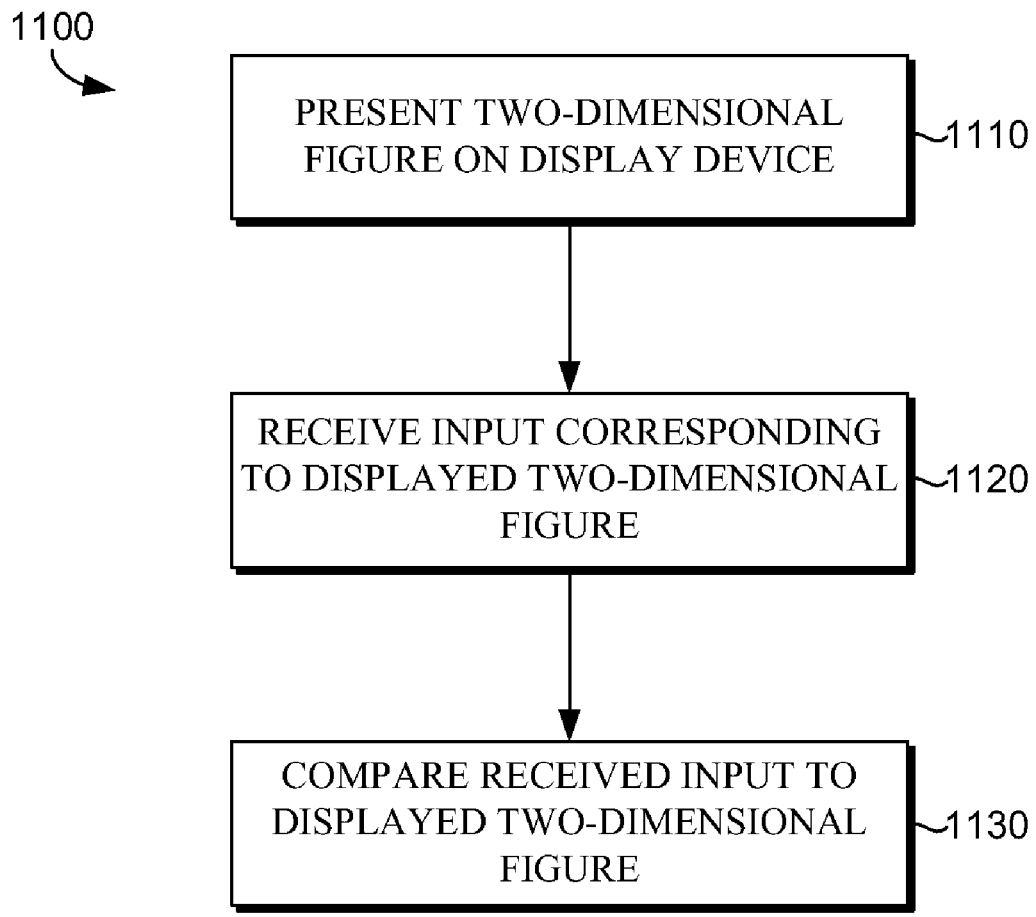
FIG. 11 illustrates a method for testing and/or training the visual perception span and/or speed of a subject in accordance with an embodiment of the present invention.

Referring now to FIG. 11, a method 1100 of testing and/or training the visual perception span and/or speed of a subject in accordance with an embodiment of the present invention. Although the terms "step" and "block" are used hereinbelow to connote different portions of methods employed, the terms should not be interpreted as implying any particular order among or between various steps herein disclosed unless and except when the order of individual steps is explicitly described.

At step 1110, visual information comprising a two-dimensional figure is presented to a subject on a display device. At step 1120, the responsive input corresponding to the displayed two-dimensional figure may then be received by an input device. In embodiments, a single touch-sensitive screen may be used as both a display device and an input device. At step 1130, a processing component may then compare the received input with the displayed two-dimensional figure. The steps of method 1100 may be performed, for example, by a computing device such as testing unit 140 shown in FIG. 1, in conjunction with one or more display device and one or more input device.

Figure 12:
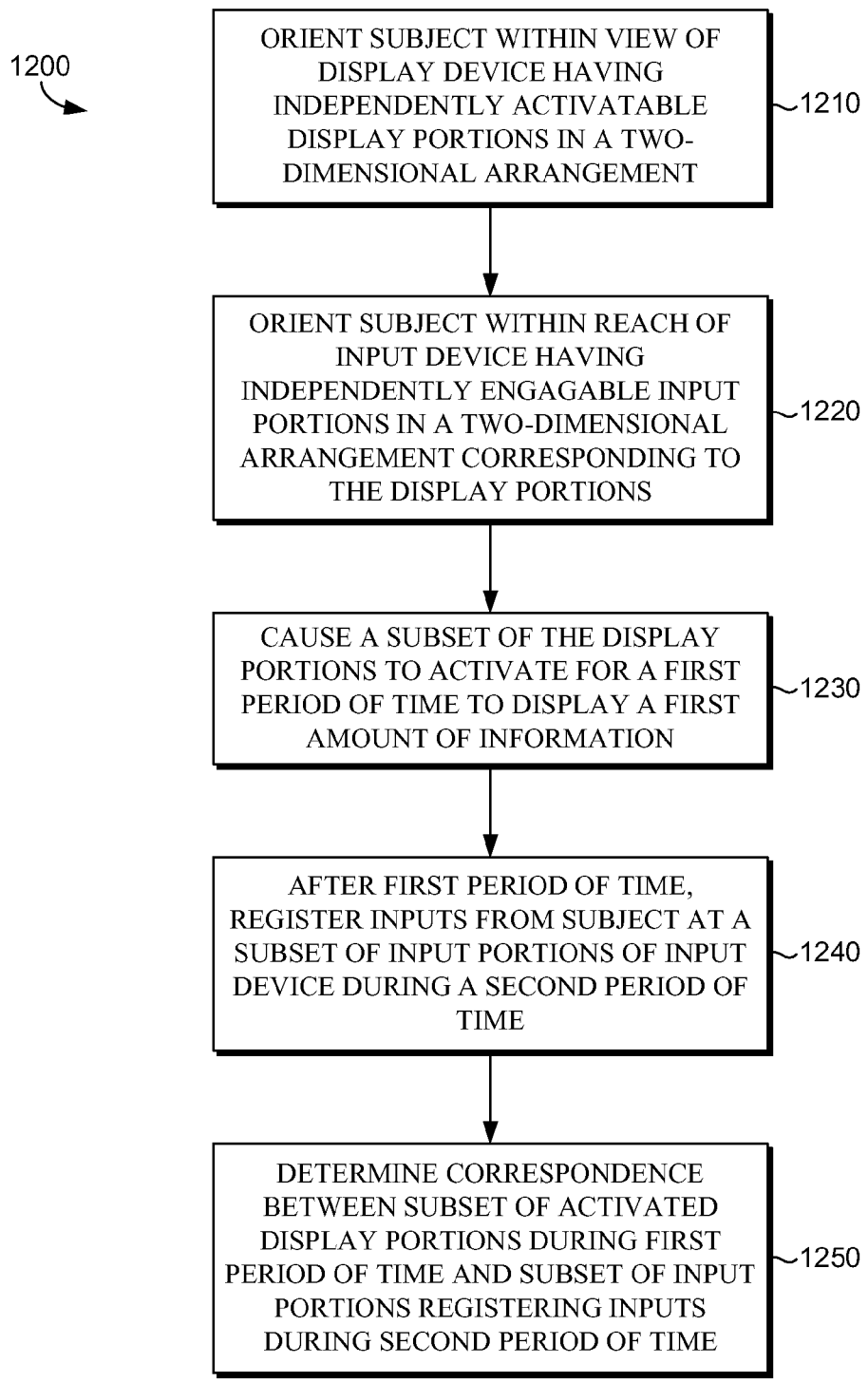
FIG. 12 illustrates another method for testing and/or training the visual perception span and/or speed of a subject in accordance with an embodiment of the invention.

FIG. 12 illustrates a method 1200 for testing and/or training the visual perception span and/or speed of a subject in accordance with an embodiment of the present invention. In step 1210, a subject may be oriented within view of a display device. The display device may have independently activatable display portions in a two-dimensional arrangement. In step 1220, the subject may be oriented within reach of an input device. The display device of step 1210 and the input device of step 1220 may comprise a single touch sensitive display device that both displays information to and receives inputs from the subject. The input device may have independently engagable input portions in a two-dimensional arrangement. The two-dimensional arrangement may correspond to the display portions of the display device. Alternatively, the two-dimensional arrangement may be more extensive than the display portions, such that the two-dimensional arrangement may correspond to the dimensions of a number of different display devices.

At step 1230, a subset of the portions of the display device may be activated for a first period of time to provide a first amount of visual information to subject. In embodiments, "period of time" may refer to a discrete amount of time. The subset may comprise display portions that may possess varied characteristics, such as different colors, different sizes, etc. The amount of information displayed during step 1230 may directly relate to the amount of portions included in the subset activated and/or the characteristics that subset possesses. After a first period of time, the inputs from the subset may be registered in an input device in step 1240. A single touch-sensitive screen may comprise both a display device and an input device. The inputs registered may comprise a subset of the input portions of a input device. Step 1240 may occur during a second period of time subsequent to the period of time of step 1230. After the expiration of the second period of time, the subject may be locked from adding any additional inputs. Once inputs have been registered on an input device, a correspondence between a subset of activated display portions and a subset of input portions may be determined based on the inputs registered during the second period of time.

Method 1200 may be repeated any number of times to test and/or train the visual perception speed and/or span of a subject. The amount of information displayed in step 1230 may vary in different iterations of method 1200 to test/train the perception span of the subject. The first period of time during which a subset of the portions of the display device are activated in step 1230 may vary in different iterations of method 1200 to test/train the perception speed of a subject.

Figure 13:
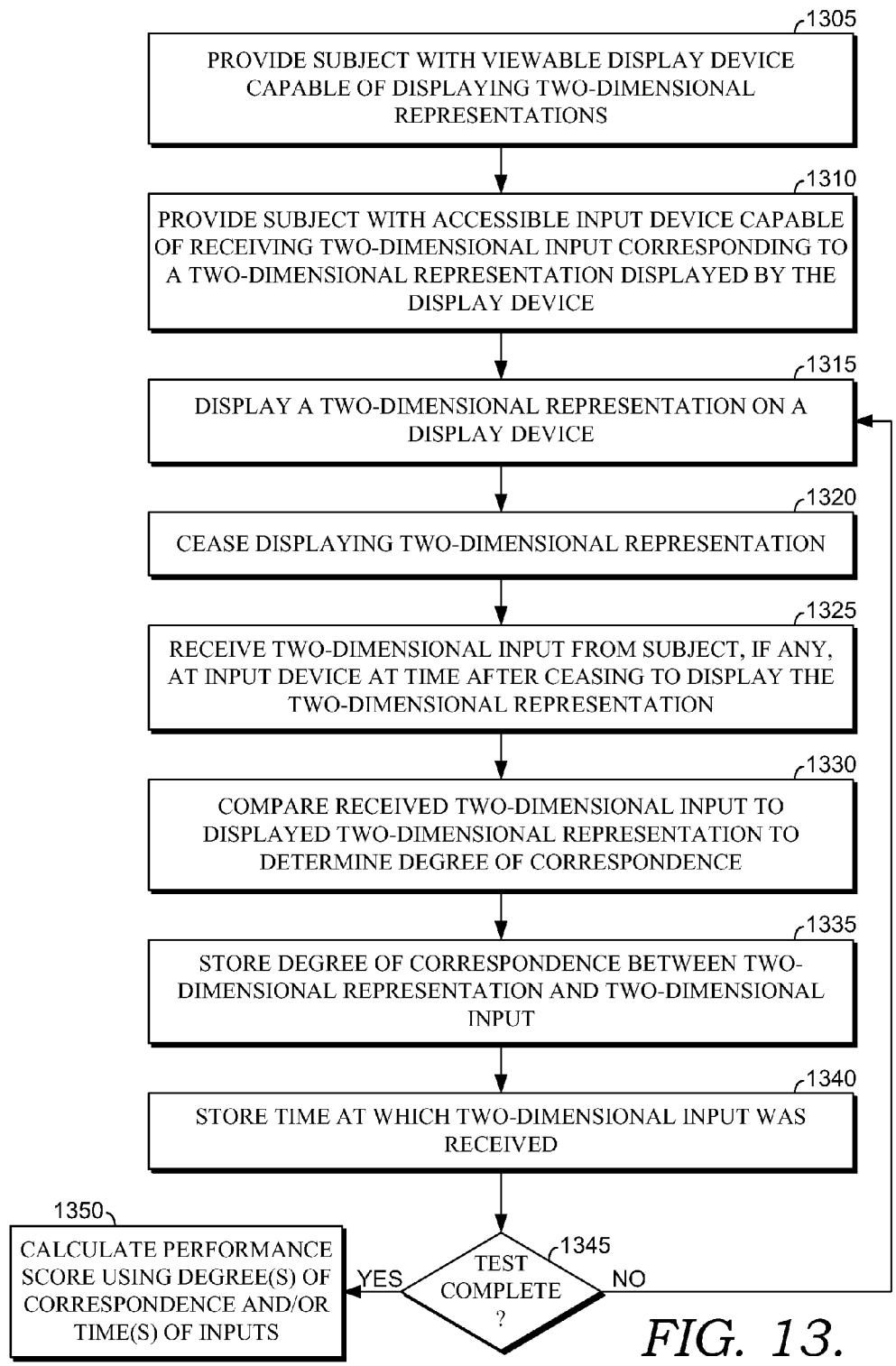
FIG. 13 illustrates a further method for testing and/or training the visual perception span and/or speed of a subject in accordance with an embodiment of the invention.

Referring to FIG. 13, a further method 1300 for testing and/or training the visual perception span and/or speed of a subject in accordance with an embodiment of the present invention. In step 1305, a subject is provided with a viewable display device capable of displaying two-dimensional representations. In step 1310, the subject is provided with an accessible input device capable of receiving two-dimensional input. A single touch-sensitive screen may comprise both a display device and an input device. Alternatively, the two-dimensional input may comprise a series of buttons and/or touch screen portions at which a subject may indicate the location on an input device that corresponds with the location at which the subject saw an active portion on the display device, and the display device may comprise any type of monitor, display, etc. In step 1315, visual information comprising a two-dimensional representation is displayed on the display device. The amount of visual information displayed in step 1315 may be controlled for testing and/or training the visual perception span of an individual. The display of the two-dimensional representation on the display device may cease in step 1320. The duration of step 1315 prior to step 1320 may be controlled for testing and/or training the visual perception speed of an individual.

In step 1325, a two-dimensional input from the subject is received at the input device. One or more responses may be input at a time after the display of the two-dimensional representation has ceased in step 1320. After the two-dimensional response inputs have been received at the input device, the responses may be compared to the two-dimensional representation displayed on the display device in step 1330. The comparison may be used to make a determination as to the degree of correspondence between the two-dimensional response inputs and the two-dimensional representation displayed on the display device. The degree of correspondence may be stored in step 1335. The degree of correspondence may be stored on a database, such as database 150 as indicated in FIG. 1. In addition, the time at which the responsive two-dimension input was received may be stored in step 1340, which may be used as a indication of quickness of a response.

At step 1345, a determination may be made as to whether the test and/or training of the visual perception span and/or speed of the subject is complete. If the test and/or training is not complete, method 1300 may return to step 1310. If, however, the test and/or training is complete, method 1300 may proceed to step 1350 and calculate a performance score using information such as, for example, the degree of correspondences between the two-dimension response inputs and the two-dimensional representations displayed on the display device. The duration of time during which visual information was displayed, the quickness of a response prior testing/training by the subject or others, etc., although only a portion of these types of information may be used.

Referring now to FIGS. 14A-14C, a system 1400 for testing and/or training the visual perception span and/or speed of a subject 1490 is illustrated. System 1400 may use a touch-sensitive screen 1440 as both a display device and an input device in testing and/or training the visual perception span and/or speed of subject 1490, which permits subject 1490 to utilize his sensory memory in testing and/or training.

Touch-sensitive screen may be rigidly affixed or adjustably attached to kiosk 1410. A control unit 1420 may connect to touch-sensitive screen via connection 1442. Control unit 1420 may comprise any type of computing device, or multiple computing devices, with a processor(s), a storage device(s), a network connection(s), etc. Connection 1442 may comprise any type of wired or wireless connection.

Control unit 1420 may cause touch-sensitive screen 1440 to display spatially arranged visual indicia, such as first indicia 1460, second indicia 1461, third indicia 1462, and fourth indicia 1463. Control unit 1420 may also receive touch inputs from touch-sensitive screen 1440, such as first selection 1470, second selection 1471, third selection 1472, and fourth selection 1473. Of course, subject 1490 may not necessarily successfully register inputs correctly corresponding to displayed visual indicia. As described above, control unit may measure both the accuracy of the selections by subject 1490 to obtain a measure of the perception span of subject 1490, and more or less visual information may be included in different testing/training iterations. Also as described above, the duration of time during which visual indicia are displayed may be varied by control unit 1420 to provide a measure of the perception speed of subject 1490. Further, the time required for subject 1490 to provide a response may be measured and recorded.

Figure 15:
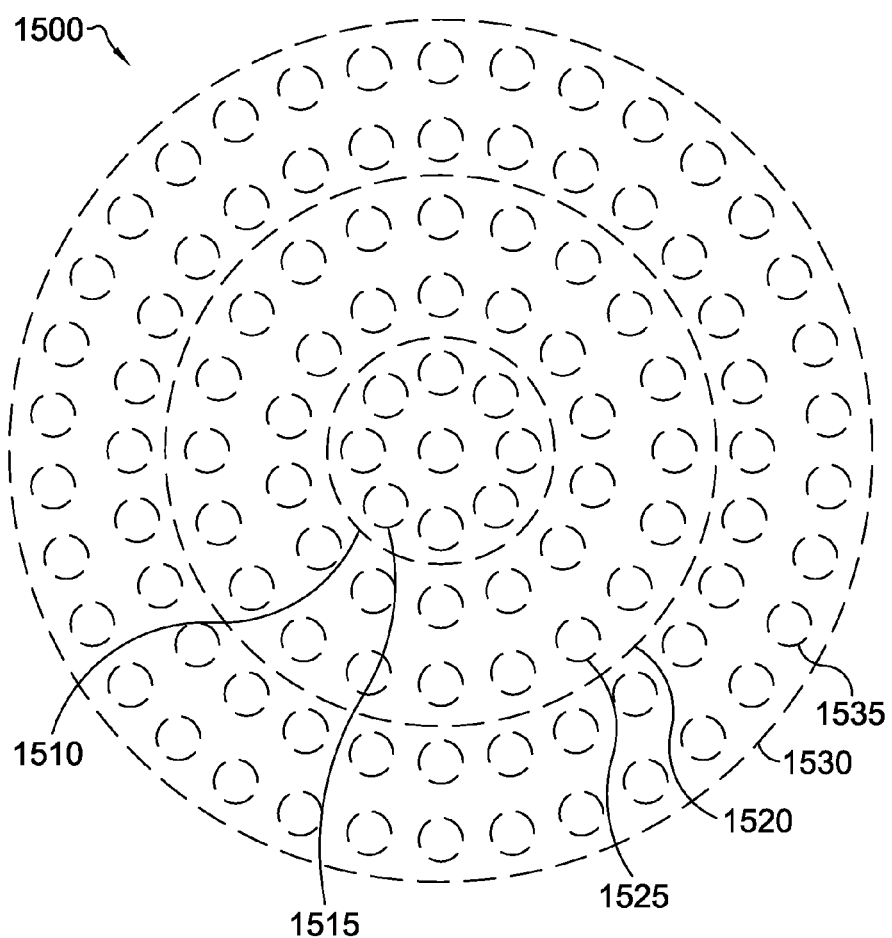
FIG. 15 illustrates an embodiment of a display device capable of displaying varying amounts of visual information for use in testing and/or training the visual perception span and/or speed of a subject.

Referring now to FIG. 15, a further embodiment of a display device capable of displaying varying amounts of visual information for use in testing and/or training the visual perception span and/or speed of a subject is illustrated. Display device 1500 may display a plurality of visual indicia in a two dimensional spatial arrangement to provide visual information to a subject. Display device 1500 may be touch sensitive, so as to enable a subject to register inputs corresponding to the information displayed at a prior time by touching the display device 1500. The indicia illustrated in the example of FIG. 15 comprise individual circles that may be active or inactive, although other types of indicia that may possess various traits beyond simply active or inactive may be used. In use, a subset of the indicia of display device 1540 may be activated for a first period of time and thereafter deactivated, at which time a subject may attempt to touch portions of display device 1500 previously activated. As illustrated in FIG. 15, indicia may be arranged in expanding concentric circles, such as first circle 1510, second circle 1520, and third circle 1530. First circle 1510 may contain a first plurality of indicia, such as first indicia 1515. Second circle 1520 may contain a second plurality of indicia, such as second indicia 1525. Third circle 1530 may include a third plurality of indicia, such as third indicia 1535. More or fewer concentric circles than the three illustrated in FIG. 15 may be used in accordance with the present invention, and any given concentric circle may contain more or fewer indicia than illustrated in FIG. 15 without departing from the scope of the present invention. The use of a plurality of concentric circles, each containing a predetermined maximum amount of possible visual information, in this case a predetermined number of indicia, the testing and/or training of the visual perception span and/or speed of a subject may be adjusted to contain more or less visual information for particular iterations by including indicia within more or fewer circles. For example, a testing session may commence using only visual indicia within the first circle 1510. After the subject has correctly responded to a predetermined number of displays of visual information within first concentric circle 1510, further testing iterations may be performed using indicia included within both first concentric circle 1510 and within second concentric circle 1520. If such testing is successful, the subject may thereafter perform testing iterations using the first concentric circle 1510, the second concentric circle 1520, and the third concentric circle 1530. Of course, testing iterations may begin using the maximum amount of possible information and reduce the presented information through the course of testing, or testing iterations may be distributed in other fashions that vary between more and less information being displayed to a subject. Similarly, the training of a subject's visual perception span and/or speed may utilize varying amounts of visual information, which may be accomplished using concentric circles such as the exemplary concentric circles illustrated herein in conjunction to FIG. 15.

Figure 16:
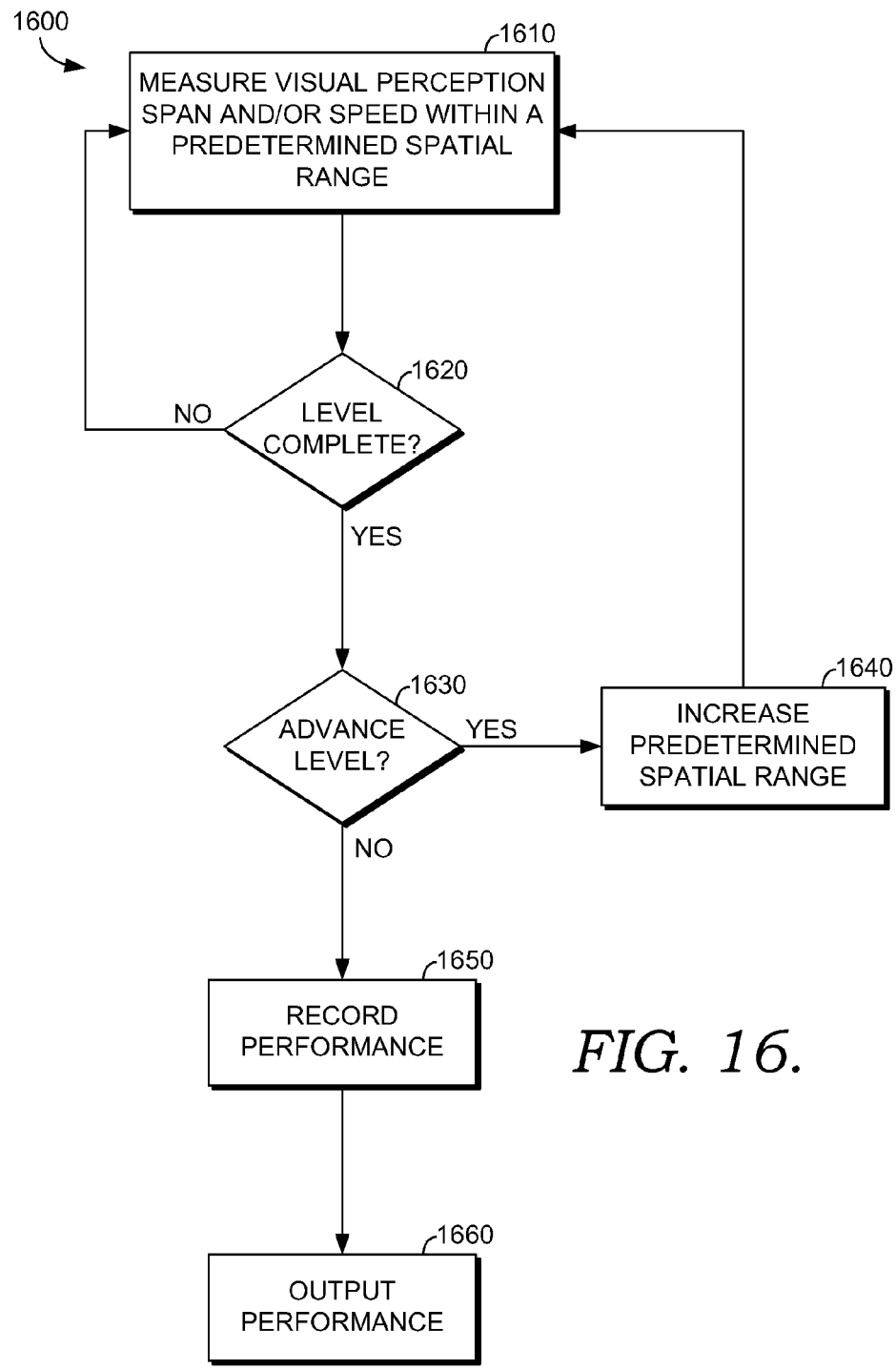
FIG. 16 illustrates a further method for testing and/or training the visual perception span and/or speed of a subject in accordance with the present invention.

Referring now to FIG. 16, a further method for testing and/or training the visual perception span and/or speed of a subject in accordance with the present invention utilizing multiple levels is illustrated. Method 1600 may utilize concentric circles of indicia, such as illustrated in FIG. 15, to vary the spatial range of information displayed in an iteration, but method 1600 may be adapted to use other displayed configurations that vary the amount of information displayed for any given iteration, the difficulty of perceiving the displayed information, the amount of time for which a given information set is displayed, or otherwise varies the difficulty of an iteration. In step 1610, the visual perception span and/or speed of a subject may be measured within a predetermined spatial range. The predetermined spatial range in step 1610 may comprise, for example, the first circle 1510 illustrated in FIG. 15. In step 1620 a determination is made as to whether the level is complete. The determination of step 1620 may be based upon criteria such as the number of iterations at an earlier level that have been performed, number of accurate responses provided at an earlier level, the accuracy of prior responses, etc. If the conclusion of step 1620 is that the level is not complete, method 1600 may return to step 1610. If the conclusion of step 1620 is that the level is complete, method 1600 may proceed to step 1630. Step 1630 determines whether to advance another level. If the conclusion of step 1630 is to advance a level, method 1600 proceeds to step 1640, which increases the predetermined visual range for visual perception span and/or speed testing/training. For example, step 1640 may increase the spatial range to include both the first circle 1510 and the second circle 1520 illustrated in FIG. 15. Thereafter, method 1600 returns to step 1610 using the increased spatial range. If the determination of step 1630 is not to advance a level, method 1600 may proceed to step 1650 of recording the performance of the subject. Of course, step 1650 may be performed contemporaneously with other measurements. Method 1600 may thereafter proceed to step 1660 of outputting the performance of a subject. Step 1660 may comprise displaying a score on a display device, printing a report of the performance of the subject, making an electronic record of the subject's performance on a local storage media or on a remote server or storage media, or any other way of providing a measure of performance of the subject for contemporaneous or subsequent use.

In accordance with the present invention, visual perception span and/or speed may be tested and/or trained using a variety of displayed visual information. For example, depictions of activity that provide visual information to a subject may be used, such as visual depiction of a football line of scrimmage during play from the perspective of a ball carrier. In this example, the subject could provide a response identifying the "hole" in the line where it would be desirable to cut to in an actual game. Of course, other depictions of activity, sporting and otherwise, may be used in accordance with the present invention.

The present invention has been described in relation to particular embodiments, which are intended in all respects to be illustrative rather than restrictive. From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and is within the scope of the claims.

The invention claimed is:

1. A system for measuring the visual perception span and/or speed of a subject, comprising:
   a display device capable of displaying a two-dimensional representation, the display device comprising a plurality of portions in a two-dimensional arrangement, each portion capable of activation independence;
   an input device capable of receiving a plurality of responsive inputs from the subject, each of the plurality of responsive inputs corresponding to a portion on the display device; and
   a test unit operably connected to the display device and the input device, the test unit operable to:
      cause the display device to display a first two-dimensional representation for a first predetermined amount of time, the first two-dimensional representation comprising a first plurality of active portions of the display device;
      cause the display device to cease to display the first two-dimensional representation after the conclusion of the first predetermined amount of time;
      cause the input device to receive, for a second period of time, any of a plurality of inputs from the subject, each of the plurality of inputs corresponding to at least one portion of the display device;
   after the second period of time, compare the plurality of inputs received by the input device during the second period of time to the first two-dimensional representation displayed by the display device during the first period of time to determine:
      which of the plurality of inputs correspond to an active portion of the first two-dimensional representation;
      which of the plurality of inputs do not correspond to an active portion of the first two-dimensional representation;
      which of the active portions of the first two-dimensional representation a corresponding input; and
      outputting the results of the comparison.

2. The system of claim 1, wherein the first plurality of active portions is fewer in number than the plurality portions capable of activation.

3. The system of claim 1, wherein the display device comprises one or more display screens.

4. The system of claim 1, wherein the display device comprises eyewear.

5. The system of claim 1, wherein the plurality of portions comprise more than one color.

6. The system of claim 1, wherein the input device is operable to receive any of a plurality of inputs from the subject immediately after the conclusion of the first period of time.

7. The system of claim 1, wherein the first period of time and the second period of time may overlap.

8. The system of claim 1, wherein the plurality of active portions comprises at least one characteristic distinct from the plurality of inactive portions.

9. The system of claim 1, a second two-dimensional representation is presented for a third period of time, wherein the third period of time is capable of overlapping at least one of the first and second periods of time.

10. The system of claim 1, wherein the display device and the input device comprise a single touch-sensitive screen.

11. A method for measuring the visual perception span and/or speed of a subject, the method comprising:
    orienting the subject within view of a display device and within reach of an input device, wherein
       the display device comprises a plurality of display portions in a two-dimensional arrangement, each of the plurality of display portions being capable of activation independent of the other display portions; and
       the input device comprises a plurality of input portions in a two-dimensional arrangement corresponding to the two-dimensional arrangement of the plurality of display portion, each of the plurality of input portions capable of registering an input independent of the other input portions;
    causing the display device to activate a subset of the plurality of display portions to render a two-dimensional representation viewable to the subject, the activation of the subset of the plurality of display portions lasting for a first period of time;
    registering any inputs provided by the subject at a subset of the plurality of input portions of the input device during a second period of time; and
    determining the amount of correspondence between the subset of display portions activated during the first period of time and the subset of the plurality of input portions registering inputs during the second period of time.

12. The method of claim 11, wherein the display device and the input device comprise the same touch-sensitive screen.

13. The method of claim 11, wherein the any inputs provided by the subject at a subset of the plurality of input portions of the input device are registered after the first period of time has been completed.

14. The system of claim 11, wherein the amount of correspondence between the subset of display portions activated during the first period of time are determined after the completion of the second period of time.

15. The system of claim 11, wherein subset of the plurality of input portions registering inputs during the second period of time are determined after the completion of the second period of time.

16. A system for testing or training the visual perception span and/or speed of a subject, the system comprising:
    a display device having a plurality of display portions arranged in a two-dimensional lattice, each of the portions capable of independent activation;
    a touch-sensitive input device having a plurality of input portions arranged in a two-dimensional lattice corresponding to the plurality of display portions on a one-to-one spatial basis, each of the input portions capable of independent receipt of an input;
    a testing unit operably connected to the display device and to the touch-sensitive input device, the testing unit operable to:
       cause the display device to activate, for a first period of time, a subset of the display portions to display a first amount of visual information in a two-dimensional figure comprised of activated display portions to the subject;
       cause the display device to cease to present the two-dimensional figure to the subject;
       cause the input device to receive for a second period of time any inputs from the subject provided to any of the plurality of input portions;
       compare any inputs received at any of the plurality of input portions during the second period of time to the subset of display portions activated during the first period of time to determine the degree of correspondence between any input received and the activated display portions.

17. The system of claim 16, wherein the display device and the input device comprise the same touch-sensitive screen.

18. The system of claim 16, wherein the display device is caused to cease to present the two-dimensional figure to the subject at the conclusion of a first period of time.

19. The system of claim 16, wherein the input device is caused to receive any inputs from the subject provided to any of the plurality of input portions after the completion of a first period of time.

20. The system of claim 16, wherein any inputs received at any of the plurality of input portions during the second period of time to the subset of display portions activated during the first period of time to determine the degree of correspondence between any input received and the activated portions are compared after the completion of a second period of time.

21. The system of claim 16, wherein the first amount of information displayed may be varied by the testing unit.

22. The system of claim 16, wherein the first period of time may be varied by the testing unit.

* * * * *